(12) United States Patent
Lee et al.

(10) Patent No.: US 11,576,765 B2
(45) Date of Patent: Feb. 14, 2023

(54) ORAL INFORMATION MANAGEMENT SYSTEM USING SMART TOOTHBRUSH

(71) Applicants: Sanggeun Lee, Gwangju-si (KR); Chaeeun Lee, Gwangju-si (KR); Jiah Lee, Gwangju-si (KR)

(72) Inventors: Sanggeun Lee, Gwangju-si (KR); Chaeeun Lee, Gwangju-si (KR); Jiah Lee, Gwangju-si (KR)

( * ) Notice: Subject to any disclaimer, the term of this patent is extended or adjusted under 35 U.S.C. 154(b) by 596 days.

(21) Appl. No.: 16/658,088

(22) Filed: Oct. 20, 2019

(65) Prior Publication Data

US 2020/0146794 A1 May 14, 2020

(30) Foreign Application Priority Data

Nov. 8, 2018 (KR) .......................... 10-2018-0136378

(51) Int. Cl.
*A61C 17/22* (2006.01)
*A61B 5/00* (2006.01)

(52) U.S. Cl.
CPC .......... *A61C 17/221* (2013.01); *A61B 5/0077* (2013.01); *A61B 5/0088* (2013.01); *A61C 17/222* (2013.01)

(58) Field of Classification Search
CPC ..... A61C 17/221; A61C 1/222; A61B 5/0077; A61B 5/0088
See application file for complete search history.

(56) References Cited

U.S. PATENT DOCUMENTS

| 2016/0113495 | A1* | 4/2016 | Nanjundappa | A61B 1/00165 |
| | | | | 433/29 |
| 2019/0313892 | A1* | 10/2019 | Deane | A61C 17/221 |
| 2020/0359777 | A1* | 11/2020 | Pesach | A61C 17/34 |

FOREIGN PATENT DOCUMENTS

| KR | 10-2018-0068703 A | 6/2018 |
| KR | 10-2018-0114570 A | 10/2018 |
| WO | 2018/086986 A1 | 5/2018 |

* cited by examiner

*Primary Examiner* — Girumsew Wendmagegn
(74) *Attorney, Agent, or Firm* — KORUS Patent, LLC; Seong Il Jeong (57) ABSTRACT

Disclosed herein is an oral information management system using a smart toothbrush, the oral information management system including: a smart toothbrush configured to include a camera and at least one sensor; and a user terminal configured to acquire information collected from the smart toothbrush; wherein the user terminal determines the oral health state of a user based on the information collected from the smart toothbrush.

4 Claims, 6 Drawing Sheets

ORAL INFORMATION MANAGEMENT SYSTEM USING SMART TOOTHBRUSH

CROSS-REFERENCE TO RELATED APPLICATION

This application claims the benefit of Korean Patent Application No. 10-2018-0136378 filed on Nov. 8, 2018, which is hereby incorporated by reference herein in its entirety.

BACKGROUND

1. Technical Field

The technical spirit of the present invention relates to an oral information management system using a smart toothbrush.

2. Description of the Related Art

Based on the numbers of outpatients and health insurance expenditures (for outpatients) of the Korean National Health Insurance in 2017, tooth-related diseases have the largest number of outpatients and the largest social expenses among Korean diseases. Although many people suffer from oral diseases as described above, prevention and management for the promotion of oral health are insufficient.

Therefore, there is a demand for the development of technology which enables individuals to directly check their oral states at home and receive medical services based on the checking.

PRIOR ART DOCUMENT

Patent Document (Patent document 1) Korean Patent No. 10-1911834 registered on Oct. 19, 2018

SUMMARY

An object of the technical spirit of the present invention is to provide an oral information management system using a smart toothbrush.

In order to accomplish the above object, the technical spirit of the present invention provides an oral information management system using a smart toothbrush, the oral information management system including: a smart toothbrush configured to include a camera and at least one sensor; and a user terminal configured to acquire information collected from the smart toothbrush; wherein the user terminal determines the oral health state of a user based on the information collected from the smart toothbrush.

The smart toothbrush may include: a body configured such that the camera and the at least one sensor are provided therein; and a bristle part configured to be separably coupled to the body.

The smart toothbrush may photograph an image of the oral cavity of the user by using the camera and detect a chemical material inside the oral cavity of the user by using the at least one sensor; and the user terminal may determine the oral health state of the user based on the photographed image and information about the detected chemical material.

The user terminal may determine the dental health state of the user based on an image of the teeth of the user and acquire information about a tooth requiring management/treatment among the teeth of the user; and may evaluate the bad breath of the user based on the information about the detected chemical material and determine the cause of the bad breath when the bad breath of the user exceeds a preset reference value.

The user terminal may transmit information about the dental health state of the user to a server; and the oral information management system may further include the server configured to match at least one dental clinic to the user based on the information about the dental health state of the user received from the user terminal, to provide information about the user to the matched dental clinic, and to provide information about the dental clinic to the user terminal.

The user terminal may transmit the personal information of the user to the server; and the server may determine a medical service required for the user based on the dental health state of the user, and may select at least one dental clinic providing the medical service based on at least one of information about the current location of the user and information about the movement path of the user.

The server may select a time span for which the user visits a dental clinic based on the movement path of the user, may predict the location of the user for the selected time span, may select a dental clinic located within a predetermined distance from the predicted location, and may provide information about the selected time span and the selected dental clinic to the user terminal.

The server may select a plurality of dental clinics located within a predetermined distance from the predicted location, may provide information about the user to the plurality of dental clinics, may provide guidance on fees, differentially set depending on the type of information to be provided to the user, to the plurality of dental clinics and request the selection of the type of the information to be provided from each of the plurality of dental clinics, may request the input of additional fees, required to provide information, to the user from each of the plurality of dental clinics, may select a first dental clinic having the largest quantity of final fees, which are the sum of the fees based on the type of the information to be provided and the additional fees from among the plurality of dental clinics, and may provide information about the first dental clinic to the user terminal.

The user terminal may acquire at least one image photographed before tooth brushing of the user, at least one image photographed during the tooth brushing of the user, and at least one image photographed after the tooth brushing of the user, may evaluate the tooth brushing method of the user based on the images, and may provide information about the improvement of the tooth brushing method to the user.

BRIEF DESCRIPTION OF THE DRAWINGS

The above and other objects, features, and advantages of the present invention will be more clearly understood from the following detailed description taken in conjunction with the accompanying drawings, in which.

DETAILED DESCRIPTION

Specific embodiments of the present invention will be described in detail below with reference to the accompanying drawings. The embodiments of the present invention are provided to more fully describe the present invention to those skilled in the art. The embodiments may be modified to various different forms, and the scope of the present invention is not limited to the following embodiments. Rather, these embodiments are provided to make the present disclosure more reliable and complete and to convey the spirit of the present invention to those skilled in the art. Furthermore, in the following drawings, the thickness or size of each layer may be exaggerated for the sake of easy description and clarity.

Throughout the specification, when any component is described as being "connected" or "coupled" to another component, it should be interpreted that the former component may be directly connected or coupled to the other component but a third component may be present between the components. In contrast, when any component is described as being directly "connected" or "coupled" to another component, it should be interpreted that a third component is not present between the components. Like reference symbols denote like component throughout the drawings. As used herein, the term "and/or" refers to the inclusion of all combinations of one or more of listed items.

In the present specification, although the terms first, second, etc. may be used to describe various members, components, regions, layers and/or sections, these members, components, regions, layers and/or sections should not be limited by these terms. These terms are used merely to distinguish one member, component, region, layer, or section from another member, component, region, layer, or section. Accordingly, a first member, component, region, layer, or section discussed below could be termed a second member, component, region, layer, or section without departing from the teachings of the present invention.

Spatially relative terms, such as "beneath," "below," "lower," "above," "upper," and the like, may be used herein for ease of description to describe the relationship between one element or feature and another element or feature as shown in the drawings. It will be understood that the spatially relative terms are intended to encompass different orientations of the element or feature in use or operation, in addition to the orientation depicted in the drawings. For example, if an element or feature in the drawings is turned over, the element described as being placed "below" another element or feature may be then placed "above" the other element or feature. Accordingly, the exemplary term "below" can encompass both orientations of above and below. When a component is oriented in another direction (when a component is rotated by 90 degrees), relative descriptions used in the present specification may be interpreted correspondingly.

The terms used herein are used merely to describe specific embodiments, and are not intended to limit the present invention. A singular expression may include a plural expression unless otherwise defined. In this application, the terms "comprise," "include," "comprising," and "including" and their derivatives are used to designate the presence of one or more features, numbers, steps, operations, components, parts or combinations thereof described in the specification, and should not be understood as excluding the presence or probability of addition of one or more different features, numbers, steps, operations, components, parts or combinations thereof.

The ideal embodiments of the present invention will be described with reference to the accompanying drawings. In the accompanying drawings, for example, the modification of illustrated shapes may be expected according to manufacturing technology and/or tolerance. Therefore, the embodiments of the present invention should not be construed as being limited to the specific shapes illustrated in the drawings, and, for example, should include shape changes caused in a manufacturing process. The embodiments of the present invention may be constructed by combining one or more of a plurality of embodiments.

An oral information management system using a smart toothbrush which will be described below may have various configurations. In this case, only necessary configurations are presented as examples. It is noted that the spirit of the present invention is not limited thereto.

In the present specification, the term "computing device" refers to any type of hardware device including at least one processor, and may be understood as encompassing a software configuration operating on a corresponding hardware device according to an embodiment. For example, a computing device may be understood as including, but not limited to, both a smartphone, tablet PC or computer, and a user client or application running on each of the devices.

Embodiments of the present invention will be described in detail below with reference to the accompanying drawings.

Figure 1:
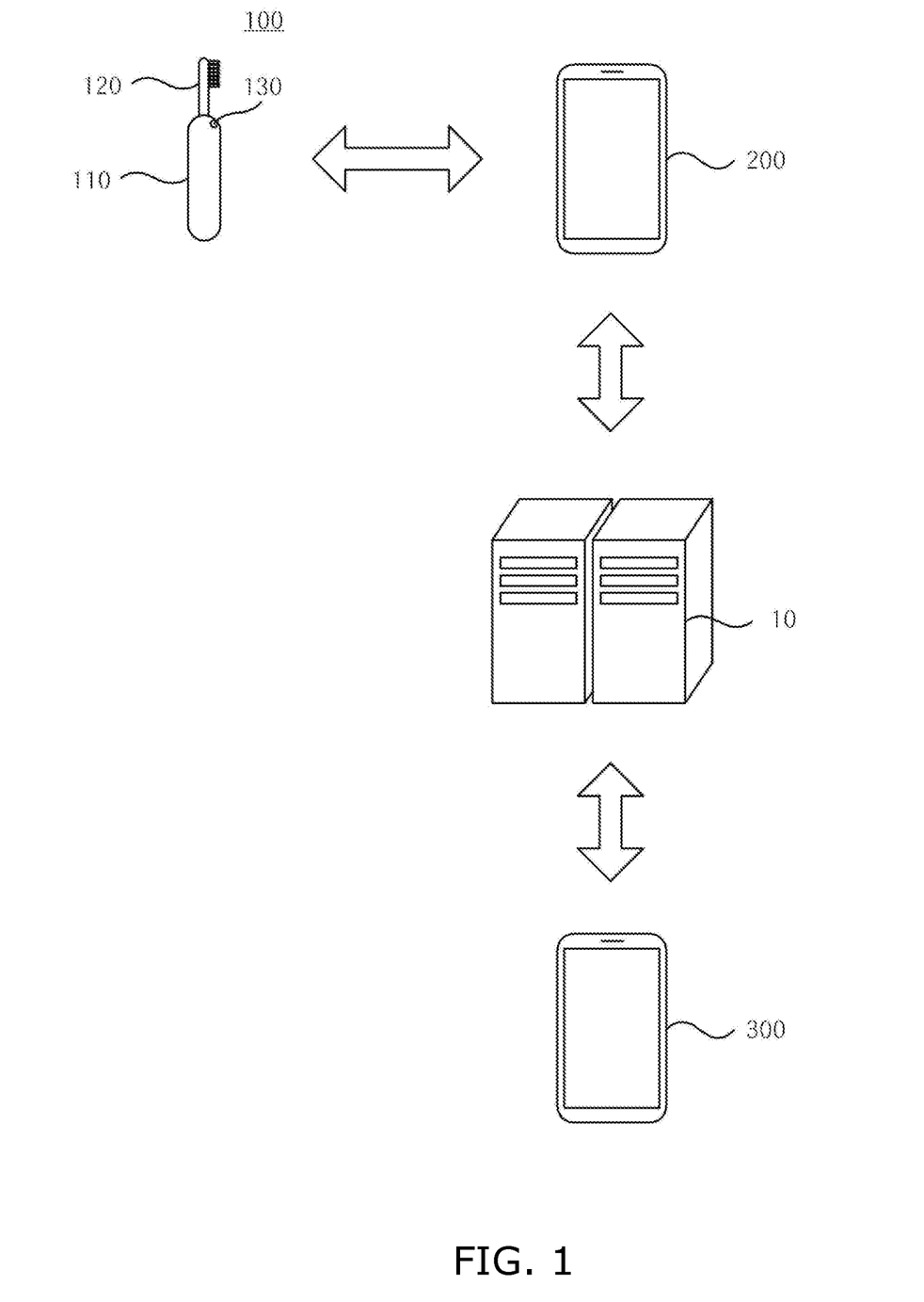
FIG. 1 is a diagram showing an oral information management system using a smart toothbrush according to an embodiment.

FIG. 1 is a diagram showing an oral information management system using a smart toothbrush according to an embodiment.

Referring to FIG. 1, there is shown the system including a smart toothbrush 100 and a user terminal 200.

Although the system may further include a server 10 and a dental clinic terminal 300 in an embodiment, it is not limited thereto. In other words, at least some of the components shown in FIG. 1 may be omitted, and one or more components not shown in FIG. 1 may be added to the system shown in FIG. 1.

Referring to FIG. 1, the smart toothbrush 100 may include a camera and at least one sensor. Referring to FIG. 1, the smart toothbrush 100 includes a body 110 and a bristle part 120, and may further include a sensor part 130 provided on the body 110 of the smart toothbrush 100.

Although the sensor part 130 may include the camera and at least one sensor in an embodiment, it is not limited thereto. Furthermore, the location of the sensor part 130 is not limited.

In an embodiment, the bristle part 120 may be configured to be separable from the body 110 and thus to be replaced with a new one when the bristle part 120 is worn. The shape of the replaceable bristle part 120 is not limited. In other words, although the replaceable bristle part 120 may be formed in a shape including a rod which is coupled to the body 110, as shown in FIG. 1, it may be formed in a shape in which the body 110 includes a rod portion rod and only bristles and a bristle mount are provided to be separably coupled to the rod portion. In this case, the sensor part 130 may be provided at at least one point (for example, near the bristle part) of the rod portion provided in the body 110.

In an embodiment, the user terminal 200 may be a type of the above-described computing device. Although the user terminal 200 is, e.g., a smartphone user, it is not limited thereto.

In an embodiment, the user terminal 200 may obtain collected information from the smart toothbrush 100. For example, the smart toothbrush 100 and the user terminal 200 may transmit and receive information in a wired or wireless manner. Although the smart toothbrush 100 and the user terminal 200 may communicate using Bluetooth as an example, it is not limited thereto.

Figure 2:
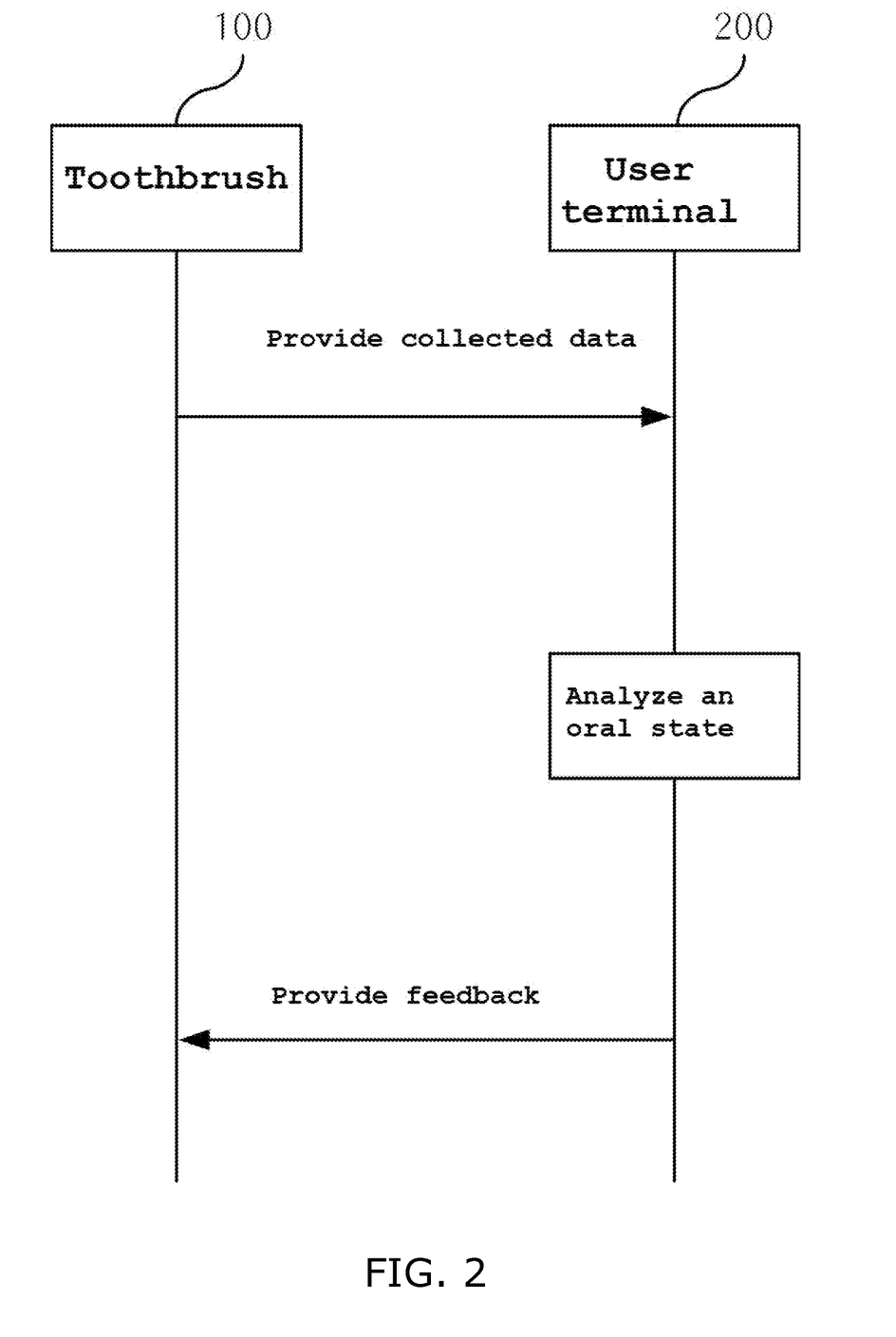
FIGS. 2 and 3 are flowcharts showing examples in which a user terminal interacts with a smart toothbrush by communicating with the smart toothbrush.
Figure 3:
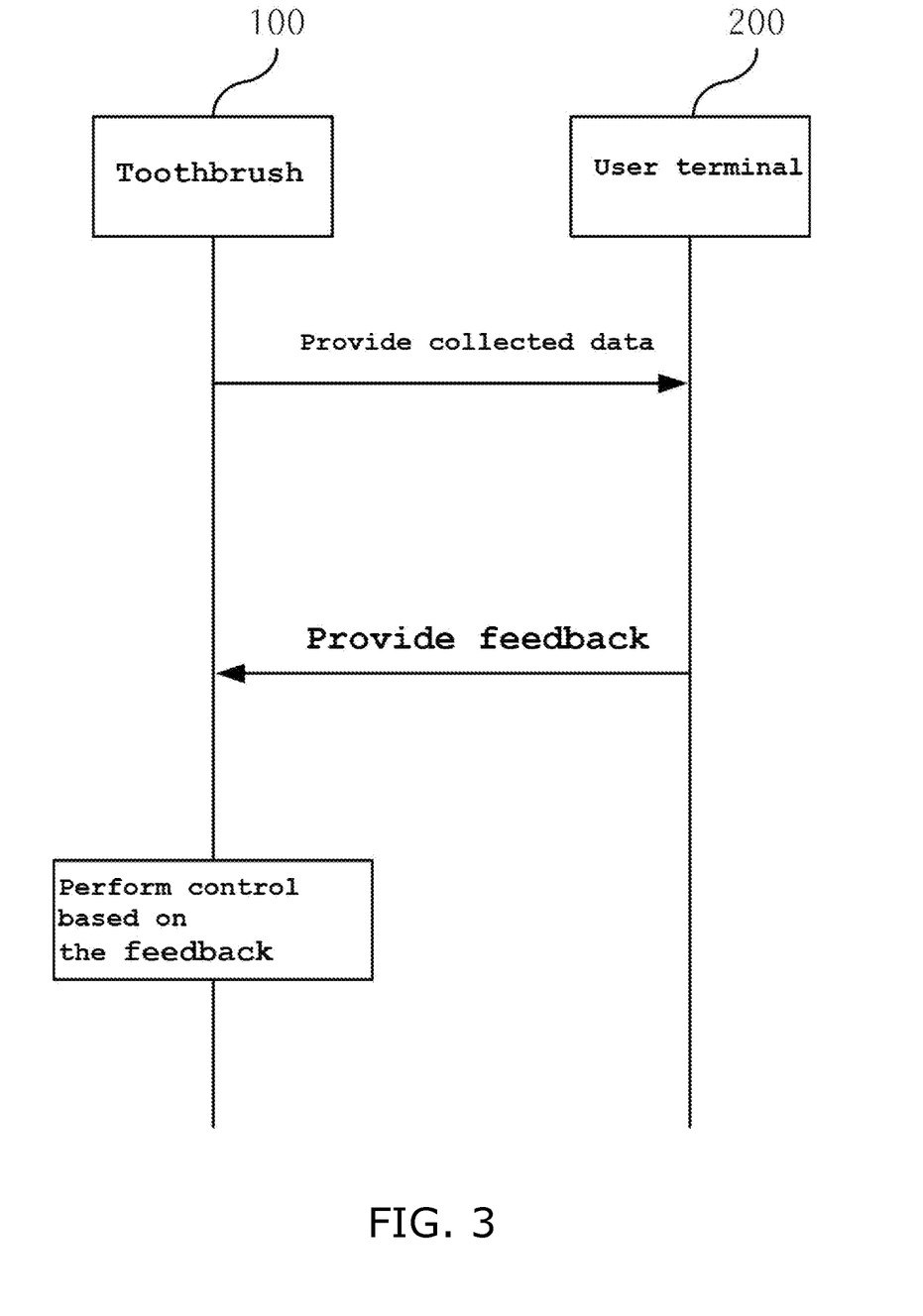

Referring to FIGS. 2 and 3, there are shown flowcharts showing examples in which the user terminal 200 interacts with the smart toothbrush 100 by communicating with the smart toothbrush 100.

In an embodiment, the smart toothbrush 100 provides data, collected via the sensor part 130, to the user terminal 200, and the user terminal 200 may analyze and determine the oral health state of a user based on the information collected from the smart toothbrush.

In an embodiment, the user terminal 200 may provide feedback to the smart toothbrush 100. The type of feedback is not limited. For example, the feedback may include information about the oral health state of the user and information about the improvement of the oral health state of the user based on the information about the oral health state.

For example, the smart toothbrush 100 may be an electric toothbrush. In this case, the user terminal 200 may provide information required to control the smart toothbrush 100 in a manner which can improve the oral state of the user based on the oral state of the user to the smart toothbrush 100.

In this case, the smart toothbrush 100 may control the bristle part based on the feedback received from the user terminal 200.

For example, when it is determined that the user has a lot of tartar, the user terminal 200 may provide information required for the smart toothbrush 100 to perform control so that the bristle part can be rotated more strongly.

Furthermore, when it is determined that the gums of the user are weak, the user terminal 200 may provide information required for the smart toothbrush 100 to perform control so that the bristle part can be rotated more weakly.

Furthermore, when it is determined that the remaining food is often left in the gap between the teeth of the user, the user terminal 200 may provide feedback, including various types of control information required to vibrate or vertically move the bristle part in order to strongly stimulate the corresponding portion, to the smart toothbrush 100.

In an embodiment, the smart toothbrush 100 may photograph an image of the oral cavity of the user by using a camera, and may detect a chemical material inside the oral cavity of the user by using at least one sensor.

For example, the smart toothbrush 100 may photograph an image including the teeth and gums of the user by using the camera. Furthermore, the smart toothbrush 100 may detect a chemical material inside the oral cavity of the user by using the at least one sensor, thereby measuring the bad breath of the user and determining the cause of the bad breath.

In an embodiment, the user terminal 200 may determine the dental health state of the user based on the image of the teeth of the user, and may acquire information about a tooth requiring management or treatment among the teeth of the user.

Furthermore, the user terminal 200 may evaluate the bad breath of the user based on information about the detected chemical material, and may determine the cause of the bad breath when the bad breath of the user exceeds a preset reference value.

In an embodiment, the user terminal 200 may determine the state of the oral cavity of the user from a photographed image by using a trained model.

For example, the artificial intelligence model may be trained using training data including a tooth image photographed by a camera and labeling information, in which information about an abnormal part of the corresponding image is indicated, and the trained artificial intelligence model may be used to estimate the state of dental health of the user from the photographed image.

In this specification, artificial intelligence technology includes machine learning technology. In particular, the artificial intelligence technology includes deep learning technology widely used to analyze images in machine learning technology. The artificial intelligence technology is not limited to a specific type of technology.

Deep learning is defined as a set of machine learning algorithms which attempt a high level of abstraction (the task of summarizing key content or functions in a large amount of data or complex data) through the combination of a plurality of nonlinear transformation techniques. Deep learning may be seen as a field of machine learning which teaches a computer how people think in a broad sense.

There are ongoing a lot of research into methods for, when there is any data, representing the data in a form which can be understood by a computer (for example, a form in which in the case of an image, pixel information is represented by column vectors) and applying the representation to training (how to make better representation techniques and how to build models to learn them). As a result of these efforts, various deep learning techniques have been developed. These deep learning techniques include a deep neural network (DNN), a convolutional deep neural network (CNN), a recursive neural network (RNN), and deep belief network (DBN).

The above description of the deep learning technology is given as an example in order to help the understanding of the artificial intelligence technology described herein, and the type of artificial intelligence technology used to determine the dental state of a user according to the disclosed embodiments is not limited thereto.

For example, all types of artificial intelligence techniques and learning methods applicable to solve the same problem by those skilled in the art may be utilized to determine the dental state of a user according to the disclosed embodiments.

In an embodiment, the user terminal 200 may determine at least one of the teeth of the user where tartar is present, the location of the tartar in the tooth, and the amount of tartar in the tooth, and may provide corresponding information. Furthermore, the user terminal 200 may evaluate at least one decayed tooth of the teeth of the user and the location and size of a decayed portion in the corresponding tooth, and may provide corresponding information.

Furthermore, the user terminal 200 may determine the bad breath of the user, and may determine the cause of the bad breath when the bad breath of the user exceeds a preset reference value. For example, the user terminal 200 may determine whether the corresponding bad breath is caused by a decayed tooth or inflammation in the mouth or by a material raised from the stomach based on the type of detected chemical material.

In a similar manner, the user terminal 200 may determine bad breath before and after the tooth brushing of the user, and may determine that the corresponding bad breath is caused by a problem of an internal organ rather than a problem of the mouth when there is bad breath even after the tooth brushing.

Furthermore, the user terminal 200 may evaluate the location and size of inflammation or a wound, the health state of the gums, and the degree of damage of the gums by analyzing the photographed image by means of an artificial intelligence model, and may provide the results of the evaluation.

In an embodiment, the user terminal 200 may acquire at least one image taken before the tooth brushing of the user, at least one image taken during the tooth brushing of the user and at least one image taken after the tooth brushing of the user, may evaluate the brushing method of the user based on the acquired images, and may provide information about how to improve the brushing method of the user.

For example, the user terminal 200 may acquire images photographed at predetermined intervals or a moving image during the tooth brushing of the user, may recognize and evaluate the tooth brushing method of the user by recognizing the movement of the bristle part for the locations of the teeth of the user, may determine a change in the health state of the teeth attributable to the tooth brushing based on the images photographed at the predetermined intervals during the tooth brushing, and, when the health state of the teeth has not improved significantly after the tooth brushing, may determine that the tooth brushing method of the user is incorrect and provide information about the improvement of the tooth brushing method.

Although the above-described operations of the user terminal 200 may be performed via an application installed on the user terminal 200, the web, SaaS, or the like, a means for the performance of the operations is not limited thereto. The user terminal 200 may display evaluation information via a display device, and may provide the evaluation information to an external terminal.

For example, the user terminal 200 may provide collected information and evaluation information based on the collected information to an external server and the smart toothbrush 100.

Figure 4:
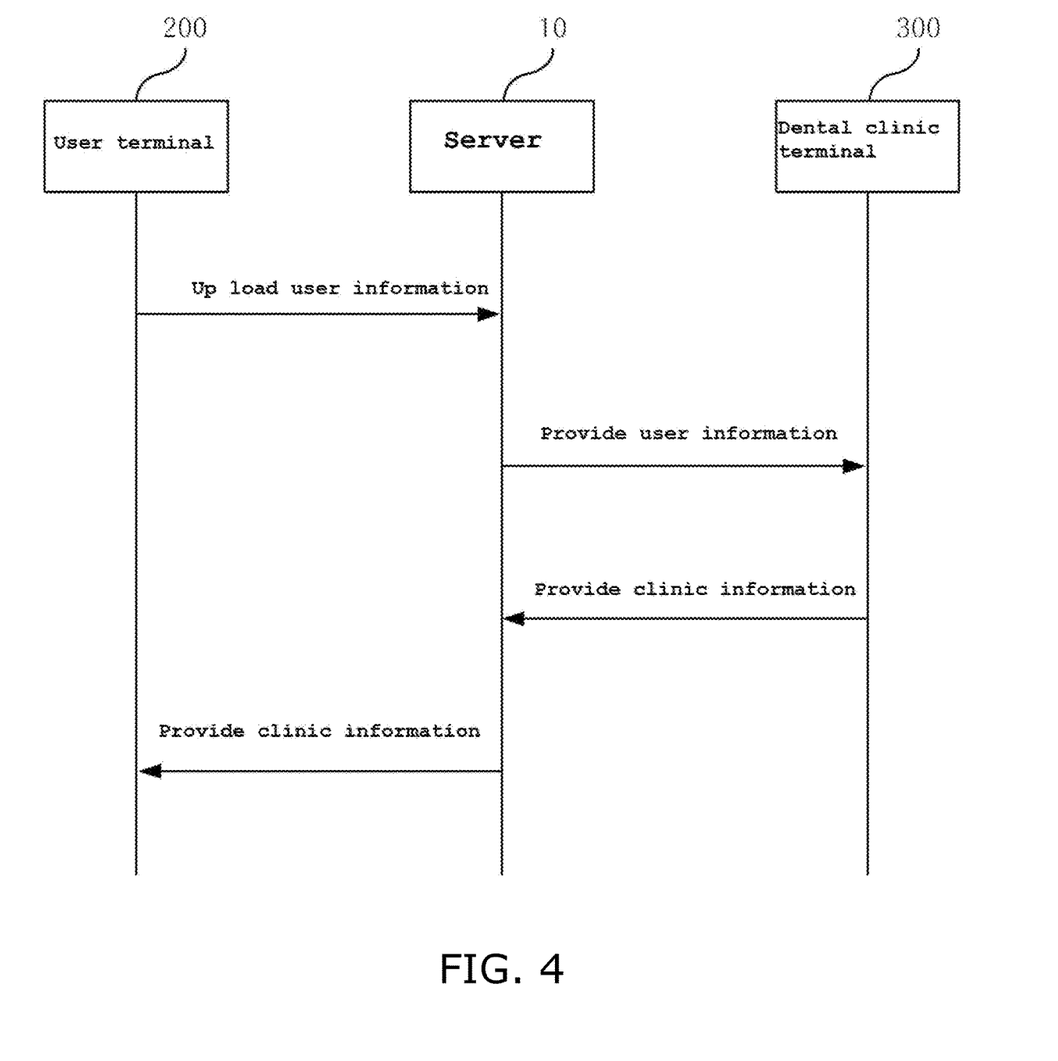
FIG. 4 is a flowchart showing the operation of a system according to an embodiment.

FIG. 4 is a flowchart showing the operation of a system according to an embodiment.

Referring to FIG. 4, the user terminal 200 may provide information about a user to the server 10, and the information about a user may include the personal information of the user and information about the dental health state of the user.

Furthermore, the server 10 may match at least one dental clinic to the user based on information about the dental health state of the user received from the user terminal 200, may provide the information about the user to the matched dental clinic, and may provide information about the dental clinic to the user terminal.

The dental clinic terminal 300 may be provided in each dental clinic. Although the dental clinic terminal 300 may refer to a management terminal installed in a dental clinic, it is not limited thereto.

Figure 5:
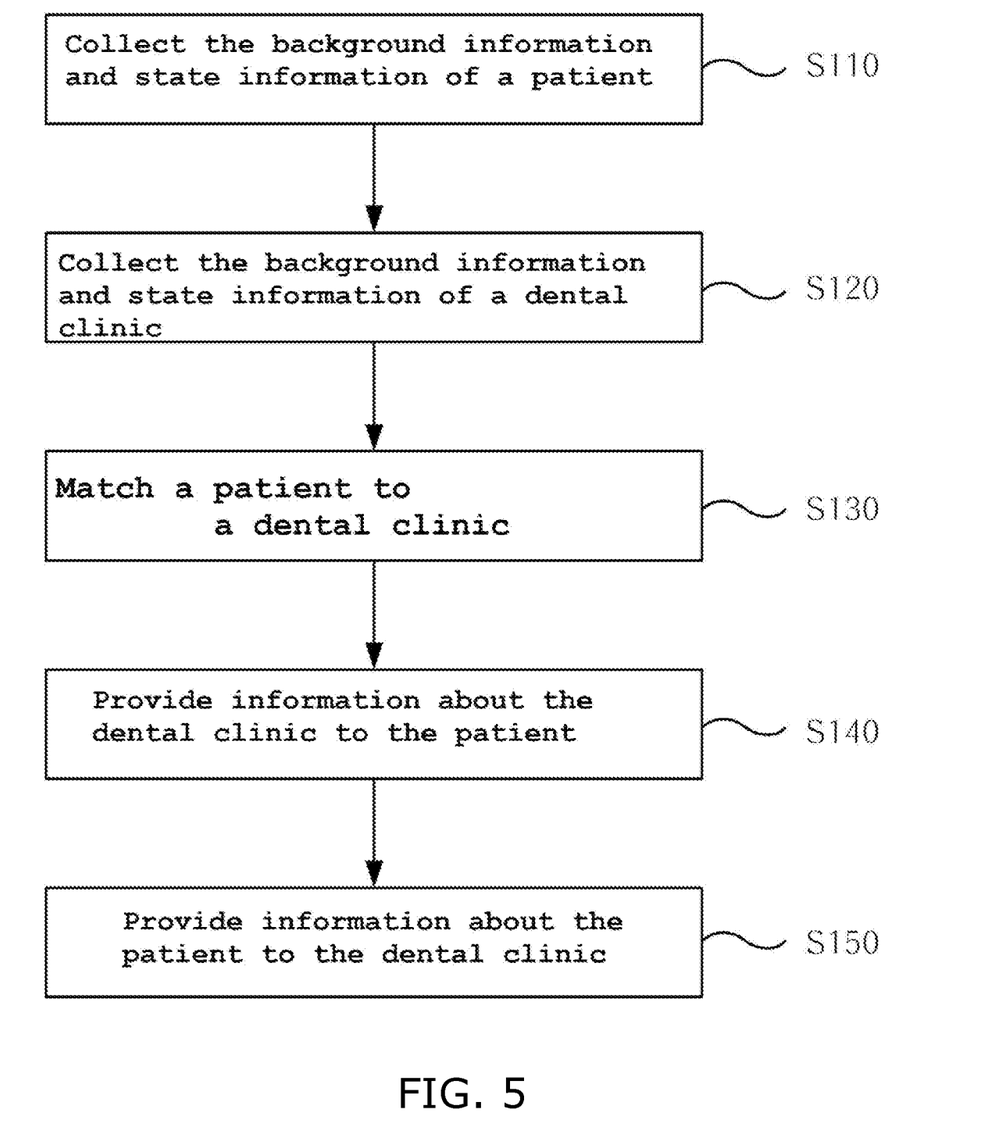
FIG. 5 is a flowchart showing a dental clinic information matching method according to an embodiment.

FIG. 5 is a flowchart showing a dental clinic information matching method according to an embodiment.

At step S110, the server 10 collects patient (user) information. The patient information includes the background information and state information of the patient.

At step S120, the server 10 collects dental clinic information. The dental clinic information includes the background information and state information of the dental clinic.

At step S130, the server 10 matches at least one patient and at least one dental clinic to each other based on the collected patient information and dental clinic information.

A method for matching a patient and a dental clinic to each other is not limited, and at least one of the above-described methods may be used as the method for matching a patient and a dental clinic to each other. A specific method according to some embodiments will be described below.

At step S140, the server 10 provides information about the matched dental clinic to the matched patient.

The type of information which is provided is not limited. For example, the information which is provided may include the location, number of patients, waiting time, medical personnel, examination and treatment information, etc. of a dental clinic. In an embodiment, the information which is provided may further include the advertising information which is provided by a dental clinic.

At step S150, the server 10 provides information about the matched patient to the matched dental clinic.

The type of information which is provided is not limited. For example, the personal information and examination and treatment information of the patient and information about the type of medical service required by the patient may be provided. Furthermore, information about a plurality of patients may be arranged and provided to a dental clinic. For example, a list of patients requiring a medical service which is provided by the corresponding dental clinic may be arranged and provided. In particular, a list of patients arranged via a predetermined filter may be provided. For example, the server 10 may provide information about patients located within a predetermined distance from the dental clinic. The location of the patient may be determined based on the current location of the patient. Information about a corresponding patient may be provided to the dental clinic even when at least part of the usual movement path of the patient is located within a predetermined distance from the dental clinic or even when at least one of the places frequently visited by the patient is located within the predetermined distance from the dental clinic.

Furthermore, the server 10 may provide information about a patient who has visited another dental clinic for the medical service or a patient who has not visited the dental clinic to the dental clinic.

In the case of the patient who has visited the dental clinic, the server 10 may determine the time at which he or she needs to re-visit the dental clinic according to the type of medical service, and may provide information about patients who have passed the time to the dental clinic. Likewise, the server 10 may provide information about the fact that the time has come, and may provide information about the corresponding dental clinic.

In one embodiment, the information about the state of the patient includes information about the current dental state of the patient and information about the current location of the patient. Furthermore, the information about the background of the patient includes information about the dental state of the patient and information about the movement path of the patient.

In an embodiment, the information about the movement path of the patient may include information about a movement path through which the patient moves periodically. For example, the movement path may include the commute path of the patient.

Furthermore, the information about the movement path of the patient may include information about a location which is frequently visited by the patient. A weight may be given to the information about the corresponding location.

For example, a higher weight may be given to a place where a patient visits and stays, such as a home, a school or a workplace, rather than a location on a subway, bus or car path.

Accordingly, when a dental clinic is recommended or patient information is provided to a dental clinic based on a movement path, a low weight may be given to a location through which a patient simply moves and passes, a high weight is given to a location which a patient actually visits, and a higher weight may be given to a location where a patient stays longer. These weights may be taken into consideration when a patient and a dental clinic are matched to each other. For example, information about a dental clinic located within a predetermined range from a location having a high weight may be provided to a patient at a high priority, and information about the corresponding patient may be provided to a dental clinic at a high priority in the same manner.

In an embodiment, the server 10 may determine a medical service, required by the patient, based on the current dental state of the patient. For example, the server 10 may determine a medical service, required by the patient, based on information collected from the smart toothbrush 100 and information analyzed by the user terminal 200. The corresponding information may be searched for by the direct input of the patient.

In an embodiment, the server 10 may select at least one dental clinic providing the medical service based on the information about the current location of the patient.

For example, the server 10 may provide information about at least one dental clinic located near the patient.

In an embodiment, the server 10 may preferentially recommend a dental clinic having a desirable review or rating among dental clinics, or may preferentially recommend a dental clinic having a short examination/treatment waiting time. The server 10 makes a reservation for a corresponding dental clinic according to the selection of the patient.

Furthermore, the server 10 may additionally provide the advertising information or event information of the dental clinic to the patient.

In another embodiment, the server 10 may determine a medical service, required by the patient, based on the dental state of the patient. For example, the server 10 may predict and determine a medical service, required by the patient, based on the existing health information of the patient, and may provide information about the corresponding medical service to the patient.

In another embodiment, the server 10 may select at least one dental clinic providing the medical service based on the movement path of the patient.

For example, the server 10 may recommend a dental clinic and provide information based on the movement path of the patient, as described above.

Figure 6:
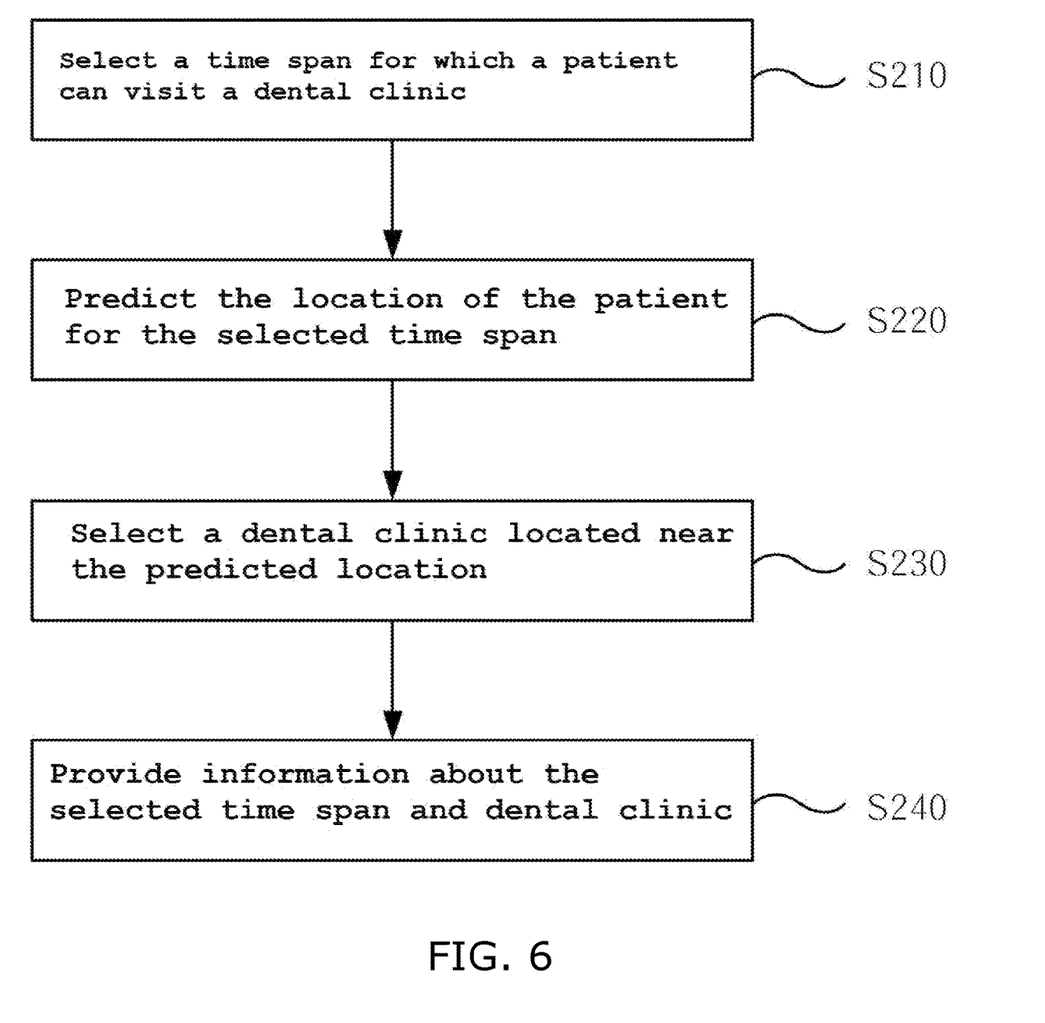
FIG. 6 is a flowchart showing a method for selecting a dental clinic and providing information according to an embodiment.

FIG. 6 is a flowchart showing a method for selecting a dental clinic and providing information according to an embodiment.

At step S210, the server 10 may select a time span for which the patient can visit the dental clinic based on the movement path of the patient.

For example, the server 10 may select the time span for which the patient can visit the dental clinic based on the ordinary movement path and location information of the patient. For example, the server 10 may select a time span before going to work, a time span after going to work, a lunchtime, a time span after work, a rest time, or the like as the time span for which the patient can visit the dental clinic.

At step S220, the server 10 predicts the location of the patient for the selected time span.

For example, the server 10 may predict the location of the patient to be a location near the home of the patient before going to work, a location near the company of the patient after going to work and before work, a location near the company of the patient during a lunchtime, or a location near the company or home of the patient after work.

At step S230, the server 10 selects a dental clinic located within a predetermined distance from the predicted location.

At step S240, the server 10 provides information about the selected time span and the selected dental clinic to the patient.

In an embodiment, the server 10 may select information about a dental clinic from which the patient can actually receive dental clinic examination/treatment for the corresponding time span based on the selected time span and the information about the average waiting time of each dental clinic for the corresponding time span, and may provide the selected information to the patient. Furthermore, the server 10 may check whether there is a reservation in each dental clinic, may obtain information about the difference between a reserved period and an actual examination/treatment period, may determine whether the patient can receive examination/treatment for the time span, selected upon reservation, based on the corresponding information, may select the corresponding dental clinic and provide information to the patient, and may inquire whether to make a reservation in the corresponding dental clinic of the patient and then make a reservation in the corresponding dental clinic according to the selection of the patient.

In an embodiment, the server 10 provides information about the patient to the selected dental clinic.

In an embodiment, the server 10 may perform the step of inquiring whether to provide the information about the patient and the type of information to be provided of the selected dental clinic.

For example, the server 10 may inquire whether to provide dental clinic information and advertising information of the corresponding patient. In an embodiment, fees may be charged for the provision of the information.

In an embodiment, the server 10 may perform the step of receiving a response to the inquiry from the selected dental clinic.

In an embodiment, the server 10 may perform the step of providing information about the selected dental clinic to the patient based on the response.

For example, when fees are paid by the dental clinic, the server 10 may provide information about the dental clinic to the patient.

In an embodiment, the server 10 may perform the step of selecting a plurality of dental clinics located within a predetermined distance from the predicted location.

In an embodiment, the server 10 may perform the step of providing information about the patient to each of the plurality of dental clinics.

In an embodiment, the server 10 may perform the step of providing guidance on fees differentially set depending on the type of information which is provided to the patient and requesting the selection of the type of information which is provided.

For example, although the information which is provided to the patient may include basic information about the dental clinic, it may further include information about an event which is provided by the dental clinic, additional information which is provided by the dental clinic, the advertising information of the dental clinic, etc. The server 10 may differentially set fees depending on the amount of information which is added.

In an embodiment, the server 10 may perform the step of requesting the input of additional fees, required to provide information to the patient, from each of the plurality of dental clinics.

For example, the server 10 may request information about additional fees which can be paid to provide fees to the patient other than the fees for the provision of additional information. The server 10 may provide information about a dental clinic which is willing to provide more additional fees to the patient. This may be performed in the form of auction or blind auction.

The auction may be performed for each patient or for a specific patient group. For example, the patient group may be classified based on a specific location, a medical service required, an age group, a gender, a movement path, or the like. Corresponding information may be provided to dental clinics.

In an embodiment, the server 10 may perform the step of selecting a first dental clinic willing to pay the largest quantity of final fees, which are the sum of the fees depending on the type of information which is provided and the additional fees, from among the plurality of dental clinics.

In one embodiment, the server 10 may perform the step of providing information about the first dental clinic to the patient.

In other words, the server 10 may select a dental clinic willing to pay the large quantity of fees to provide information to the patient, and may provide information about the corresponding dental clinic to the patient.

In an embodiment, the server 10 may request the selection of a fee payment option from the first dental clinic. The fee payment option may include a prepaid fee payment option and a postpaid fee payment option.

The server 10 may receive information about the selection of the fee payment option from the first dental clinic.

When the prepaid fee payment option is selected, the server 10 may perform the step of determining whether prepaid fees have been paid by the first dental clinic and the step of providing information about the first dental clinic to the patient when it is determined that the prepaid fees have been paid.

In other words, in the case of the prepaid fee payment option, when the overall fees have been paid, information is provided to the patient. In other words, when a dental clinic pays a deposit in advance, the server 10 may immediately process prepaid fees within the range of the deposit.

When the postpaid fee payment option is selected, the server 10 may perform the step of providing information about the first dental clinic to the patient and determining whether the patient has visited the first dental clinic and has received examination/treatment and the step of requesting the payment of postpaid fees from the first dental clinic.

In other words, in the case of the postpaid fee payment option, when examination/treatment has been actually performed, fees are paid to the server 10 on a postpaid basis. In this case, payment may be performed based on a deposit.

In the present embodiment, the postpaid fees may be characterized by being set to a higher level than the prepaid fees.

In other words, in the case of postpaid fees, fees are paid only when examination/treatment has been actual performed, and instead fees may be set to a higher level than prepaid fees. In an embodiment, the additional fees of the postpaid fees may be set as a percentage of an actual examination/treatment profit.

In an embodiment, the server 10 inquires whether to exclusively provide information of the first dental clinic. In this case, information about fees required for the exclusive provision of information may be provided.

In other words, the server 10 may inquire whether to provide only information about the first dental clinic, exclusive of information about another dental clinic, to the patient of the first dental clinic. The server 10 may charge fees in return for the exclusive provision of information.

When information about the selection of the exclusive provision of information is received from the first dental clinic, the server 10 may perform the step of providing only information about the first dental clinic to the patient.

In other words, when the first dental clinic selects the exclusive provision of information, the server 10 may provide only information about the first dental clinic to the patient.

According to an embodiment, in this case, the server 10 may request the first dental clinic to select a prepaid option or a postpaid option.

When the first dental clinic does not select the exclusive provision of information, the server 10 may provide information about each of the plurality of dental clinics to the patient.

Furthermore, the server 10 may provide pieces of information about the plurality of dental clinics to the patient in descending order of the final fees.

In other words, when the first dental clinic does not select the exclusive provision of information, the server 10 provides a plurality of pieces of dental clinic information to be paid for to the patient. The priority of the provision of information may be set in descending order of paid fees.

In this case, the server 10 may request only a prepaid option from each dental clinic. The server 10 may enable both a prepaid option and a postpaid option.

According to an embodiment, the prepaid option or postpaid option may be uniformly applied to all of the plurality of dental clinics, in which case the selection may be made by the first dental clinic. However, when the postpaid option is selected, the fees of the postpaid option may be set to a level higher than or equal to that of the fees of the prepaid option which the plurality of dental clinics could pay. The server 10 may provide information about fees based on the postpaid option to the plurality of dental clinics, and may re-inquire whether to provide information about the patient.

In the present embodiment, fees required for the exclusive provision of information are characterized by being set to a higher level than the sum of the final fees of the plurality of dental clinics except for the first dental clinic. In other words, the first dental clinic may prevent the provision of the information of other dentists and request the exclusive provision of information from the server 10 by paying all prepaid fees which the other dental clinics could pay or by paying additional fees in addition to the prepaid fees.

The steps of at least some of the methods or algorithms described in connection with the embodiments of the present invention may be implemented directly as hardware, as a software module executed by hardware, or as a combination of the two. A software module may reside in Random Access Memory (RAM), Read-Only Memory (ROM), Erasable Programmable ROM (EPROM), Electrically Erasable Programmable ROM (EEPROM), flash memory, a hard disk, a removable disk, CD-ROM, or any other form of computer-readable storage medium known in the art to which the present invention pertains.

The components of the present invention may be implemented as a program (or an application) and stored in a medium in order to be combined with a computer, i.e., hardware, and be then executed. The components of the present invention may be implemented as software programming or software elements. Similarly, the embodiments may be implemented in a programming or scripting language, such as C, C++, Java, an assembler, or the like, including various algorithms implemented in combinations of data structures, processes, routines, or other programming components. The functional aspects may be implemented as an algorithm running on one or more processors.

The smart toothbrush and the oral cavity information management system including the smart toothbrush according to the technical spirit of the present invention have the effects of enabling a user to check his or her dental state, receiving information about the improvement of the dental state, and assisting in receiving an appropriate medical service.

The above description is merely illustrative of the technical spirit of the present invention, and those skilled in the art to which the present invention pertains may make various modifications and changes without departing from the essential features of the present invention.

Therefore, the embodiments disclosed in the present invention are not intended to limit the technical spirit of the present invention but are intended to describe the present invention. The scope of the technical spirit of the present invention is not limited by these embodiments. The scope of protection of the present invention should be defined by the following claims, and all technical spirits falling within the scope equivalent thereto should be construed as being included in the scope of the present invention.

What is claimed is:

1. An oral information management system using a smart toothbrush, the oral information management system comprising:
   a smart toothbrush configured to include a camera and at least one sensor; and
   a user terminal configured to acquire information collected from the smart toothbrush;
   wherein the user terminal determines an oral health state of a user based on the information collected from the smart toothbrush,
   wherein:
   the smart toothbrush photographs an image of an oral cavity of the user by using the camera, and detects a chemical material inside the oral cavity of the user by using the at least one sensor; and
   the user terminal determines the oral health state of the user based on the photographed image and information about the detected chemical material,
   wherein the user terminal:
   determines a dental health state of the user based on an image of teeth of the user, and acquires information about a tooth requiring management/treatment among the teeth of the user; and
   evaluates bad breath of the user based on the information about the detected chemical material, and determines a cause of the bad breath when the bad breath of the user exceeds a preset reference value,
   wherein:
   the user terminal transmits information about the dental health state of the user to a server; and
   the oral information management system further comprises the server configured to match at least one dental clinic to the user based on the information about the dental health state of the user received from the user terminal, to provide information about the user to the matched dental clinic, and to provide information about the dental clinic to the user terminal,
   wherein:
   the user terminal transmits personal information of the user to the server; and
   the server determines a medical service required for the user based on the dental health state of the user, and selects at least one dental clinic providing the medical service based on at least one of information about a current location of the user and information about a movement path of the user,
   wherein the server selects a time span for which the user visits a dental clinic based on the movement path of the user, predicts a location of the user for the selected time span, selects a dental clinic located within a predetermined distance from the predicted location, and provides information about the selected time span and the selected dental clinic to the user terminal.

2. The oral information management system of claim 1, wherein the smart toothbrush comprises:
   a body configured such that the camera and the at least one sensor are provided therein; and
   a bristle part configured to be separably coupled to the body.

3. The oral information management system of claim 1, wherein the server:
   selects a plurality of dental clinics located within a predetermined distance from the predicted location;
   provides information about the user to the plurality of dental clinics;
   provides guidance on fees, differentially set depending on a type of information to be provided to the user, to the plurality of dental clinics, and requests a selection of a type of the information to be provided from each of the plurality of dental clinics;
   requests input of additional fees, required to provide information, to the user from each of the plurality of dental clinics;
   selects a first dental clinic having a largest quantity of final fees, which are a sum of the fees based on the type of the information to be provided and the additional fees from among the plurality of dental clinics; and
   provides information about the first dental clinic to the user terminal.

4. The oral information management system of claim 1, wherein the user terminal acquires at least one image photographed before tooth brushing of the user, at least one image photographed during the tooth brushing of the user, and at least one image photographed after the tooth brushing of the user, evaluates a tooth brushing method of the user based on the images, and provides information about improvement of the tooth brushing method to the user.

* * * * *